US008465503B2

(12) United States Patent
Gaynor et al.

(10) Patent No.: US 8,465,503 B2
(45) Date of Patent: Jun. 18, 2013

(54) FINGER GUIDED SUTURE FIXATION SYSTEM

(75) Inventors: Allen Gaynor, Coon Rapids, MN (US); Michael K. Luk, Hopkins, MN (US); Steven McClurg, Roseville, MN (US); Michael M. Witzmann, Minneapolis, MN (US); Ying Zheng, Stamford, CT (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 12/817,198

(22) Filed: Jun. 17, 2010

(65) Prior Publication Data

US 2011/0092985 A1    Apr. 21, 2011

(30) Foreign Application Priority Data

Oct. 19, 2009 (DK) .................................. 2009 70161

(51) Int. Cl.
*A61B 17/04* (2006.01)

(52) U.S. Cl.
USPC .......................................... 606/144; 606/139

(58) Field of Classification Search
USPC .................. 606/139, 144, 145, 148, 232; 2/21
See application file for complete search history.

(56) References Cited

U.S. PATENT DOCUMENTS

| 622,386 | A | | 4/1899 | Peery | |
|---|---|---|---|---|---|
| 2,738,790 | A | * | 3/1956 | Todt, Sr. et al. | 606/145 |
| 4,177,813 | A | * | 12/1979 | Miller et al. | 606/139 |
| 4,235,238 | A | * | 11/1980 | Ogiu et al. | 606/145 |
| 4,465,070 | A | * | 8/1984 | Eguchi | 606/145 |
| 4,620,528 | A | | 11/1986 | Arraval | |
| 4,726,371 | A | * | 2/1988 | Gibbens | 606/174 |
| 4,985,038 | A | * | 1/1991 | Lyell | 606/148 |
| 5,202,710 | A | | 4/1993 | Perkins | |
| 5,431,666 | A | | 7/1995 | Sauer et al. | |
| 5,447,512 | A | | 9/1995 | Wilson et al. | |
| 5,626,614 | A | * | 5/1997 | Hart | 606/232 |
| 5,700,273 | A | * | 12/1997 | Buelna et al. | 606/148 |
| 5,713,905 | A | * | 2/1998 | Goble et al. | 606/80 |
| 5,746,763 | A | | 5/1998 | Benderev et al. | |

(Continued)

FOREIGN PATENT DOCUMENTS

DE    2910410    12/1979
EP    1750630    2/2007

(Continued)

OTHER PUBLICATIONS

Office Action in corresponding DK application No. PA 2010 70272, dated Jan. 21, 2011.

(Continued)

*Primary Examiner* — Darwin Erezo
(74) *Attorney, Agent, or Firm* — Coloplast Corp., Coloplast A/S; Nick Baumann

(57) ABSTRACT

A suture fixation system includes a suture assembly having an anchor, an introducer, and a delivery device. The introducer is attachable to a finger of a person and includes a platform attached to an exterior of the introducer and a zip line attached to the platform. The delivery device is movable along the zip line and configured to removably retain the anchor. The introducer allows the finger to identify a target landmark within a patient and the delivery device is movable along the zip line and attachable to the platform to position the anchor for insertion to the target landmark.

11 Claims, 14 Drawing Sheets

U.S. PATENT DOCUMENTS

| | | | |
|---|---|---|---|
| 5,836,314 | A | 11/1998 | Benderev et al. |
| 5,836,315 | A | 11/1998 | Benderev et al. |
| 5,836,956 | A * | 11/1998 | Buelna et al. ............. 606/148 |
| 5,842,478 | A | 12/1998 | Benderev et al. |
| 5,860,425 | A | 1/1999 | Benderev et al. |
| 5,925,064 | A | 7/1999 | Meyers et al. |
| 6,056,688 | A | 5/2000 | Benderev et al. |
| 6,077,216 | A | 6/2000 | Benderev et al. |
| 6,231,561 | B1 | 5/2001 | Frazier et al. |
| 6,332,888 | B1 | 12/2001 | Levy et al. |
| 6,334,446 | B1 | 1/2002 | Beyar |
| 6,387,041 | B1 | 5/2002 | Harari et al. |
| 6,475,135 | B1 * | 11/2002 | Levy ............................ 600/30 |
| 6,551,330 | B1 | 4/2003 | Bain et al. |
| 6,884,249 | B2 * | 4/2005 | May et al. ............... 606/148 |
| 6,896,681 | B1 * | 5/2005 | Watson ................... 606/125 |
| 6,911,034 | B2 * | 6/2005 | Nobles et al. ............ 606/144 |
| 7,410,460 | B2 | 8/2008 | Benderev |
| 7,819,800 | B2 | 10/2010 | Beckman et al. |
| 2003/0236535 | A1 | 12/2003 | Onuki et al. |
| 2004/0260281 | A1 * | 12/2004 | Baxter et al. .............. 606/41 |
| 2005/0251208 | A1 | 11/2005 | Elmer et al. |
| 2006/0047285 | A1 * | 3/2006 | Fields ..................... 606/108 |
| 2006/0260618 | A1 | 11/2006 | Hodroff et al. |
| 2007/0239208 | A1 * | 10/2007 | Crawford ................ 606/232 |
| 2008/0196729 | A1 | 8/2008 | Browning |
| 2008/0243177 | A1 | 10/2008 | Oren et al. |
| 2008/0243178 | A1 | 10/2008 | Oren et al. |
| 2008/0311543 | A1 | 12/2008 | Viscomi et al. |
| 2011/0092986 | A1 * | 4/2011 | Gaynor et al. ............ 606/139 |
| 2011/0092987 | A1 * | 4/2011 | Gaynor et al. ............ 606/139 |
| 2011/0092991 | A1 * | 4/2011 | Gaynor et al. ............ 606/148 |

FOREIGN PATENT DOCUMENTS

| | | |
|---|---|---|
| WO | 9800069 | 1/1998 |
| WO | 0189360 A2 | 11/2001 |
| WO | 2005070305 A1 | 8/2005 |
| WO | 2007146784 | 12/2007 |

OTHER PUBLICATIONS

Office Action mailed on Mar. 28, 2011 in U.S. Appl. No. 12/905,103.
Office Action mailed on Aug. 31, 2011 in U.S. Appl. No. 12/905,103.
Office Action mailed on Oct. 27, 2011 in US U.S. Appl. No. 12/905,089.
Office Action mailed on Apr. 24, 2012 in U.S. Appl. No. 12/581,893.

* cited by examiner

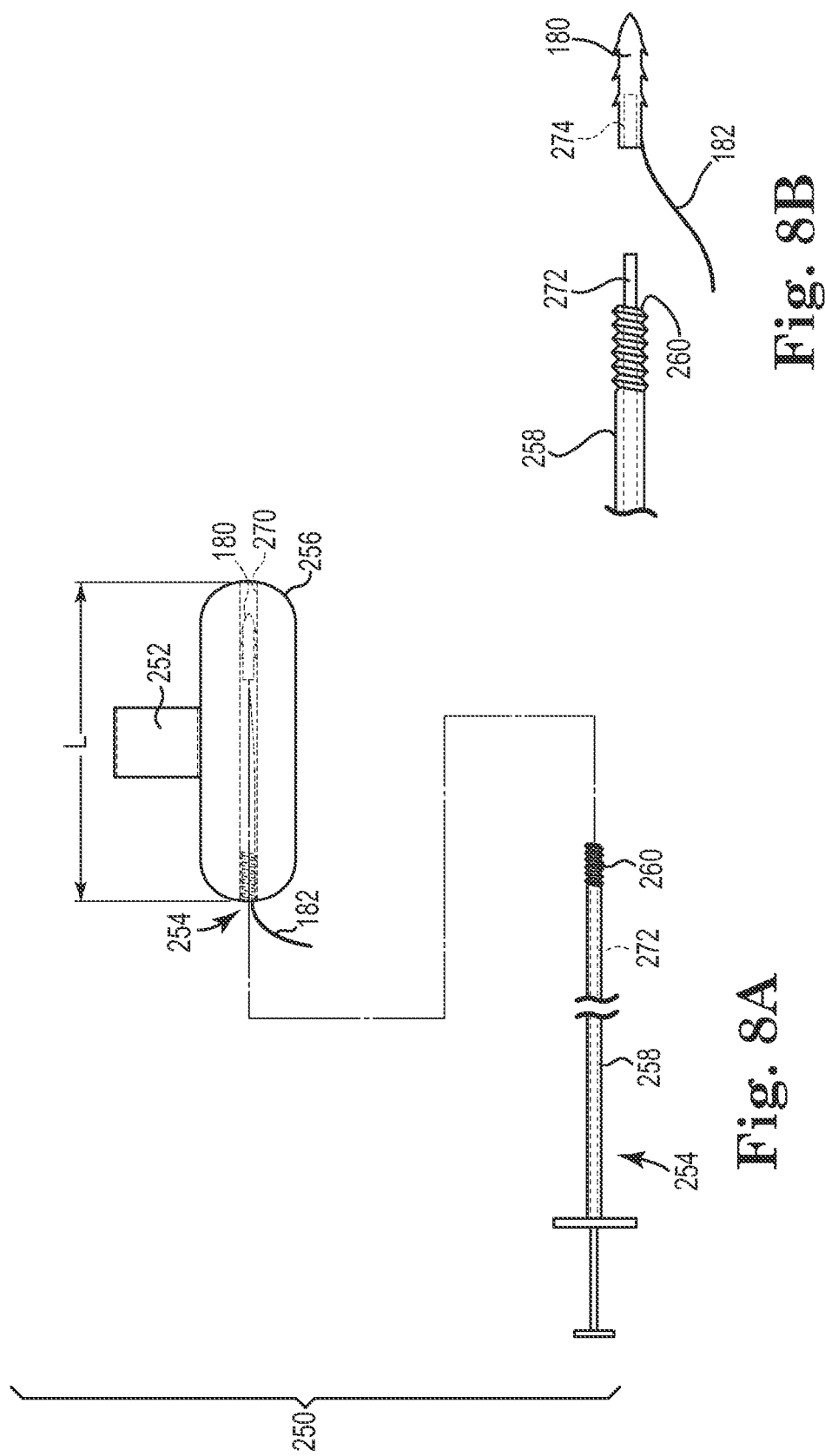

FINGER GUIDED SUTURE FIXATION SYSTEM

BACKGROUND

Intracorporeal suturing of tissue during surgery presents challenges to the surgeon in that the surgeon is called upon to manipulate one or more suturing instruments within the confines of an incision formed in the patient's body. In some cases, the surgeon will use his/her finger(s) to dissect tissue or separate tissue along tissue planes to form a space within the tissue that allows the surgeon to palpate and identify a desired target location for placement of a suture. Often, the space formed in the dissected tissue is opened until it is large enough to receive both the surgeon's finger(s) and the suturing instrument(s). The space provides access to the identified target location where it is desired to place the suture. However, the target location is often disposed inside the patient's body at an angle that is difficult to reach and can have a depth that precludes visualization of the target location. Delivering surgical instruments to the target location is challenging when the target location cannot be visualized by the surgeon.

SUMMARY

One aspect provides a suture fixation system including a suture assembly having an anchor, an introducer, and a delivery device. The introducer is attachable to a finger of a person and includes a platform attached to an exterior of the introducer and a zip line attached to the platform. The delivery device is movable along the zip line and configured to removably retain the anchor. The introducer allows the finger to identify a target landmark within a patient and the delivery device positions the anchor for insertion to the target landmark.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 8A is an exploded side view of the system illustrated in FIG. 7.

FIG. 8B is a schematic exploded view of a cable engaging with an anchor assembly of the system illustrated in FIG. 8A according to one embodiment.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

A digital suture fixation system is a system that allows suture line to be thrown through tissue and/or allows the placement of an anchor into the tissue with a hand or one or more fingers on the hand. A digital suture fixation system allows for the "finger tack" fixation of suture line and/or anchors into the tissue.

Embodiments provide a finger guided suture fixation system that includes an introducer that is configured to be donned over a finger of a surgeon to allow the finger to palpate and identify a landmark within the patient, and a delivery device configured to insert an anchor at the identified landmark. As an example, the introducer is provided with a zip line that is sized to trail proximally behind the finger to a location outside of the patient's body. The delivery device is movable along the zip line and attachable to the introducer. In this manner, the surgeon is able to locate a target site of interest with his/her finger and pass the delivery device along the zip line to the finger until it is placed at or near the target site to allow the precise placement of the anchor even without visually seeing the target site.

In this specification, "zip line" means a conduit, such as a cable, that provides a pathway from a location exterior a patient's body to a location intracorporeal the patient's body.

Figure 1:
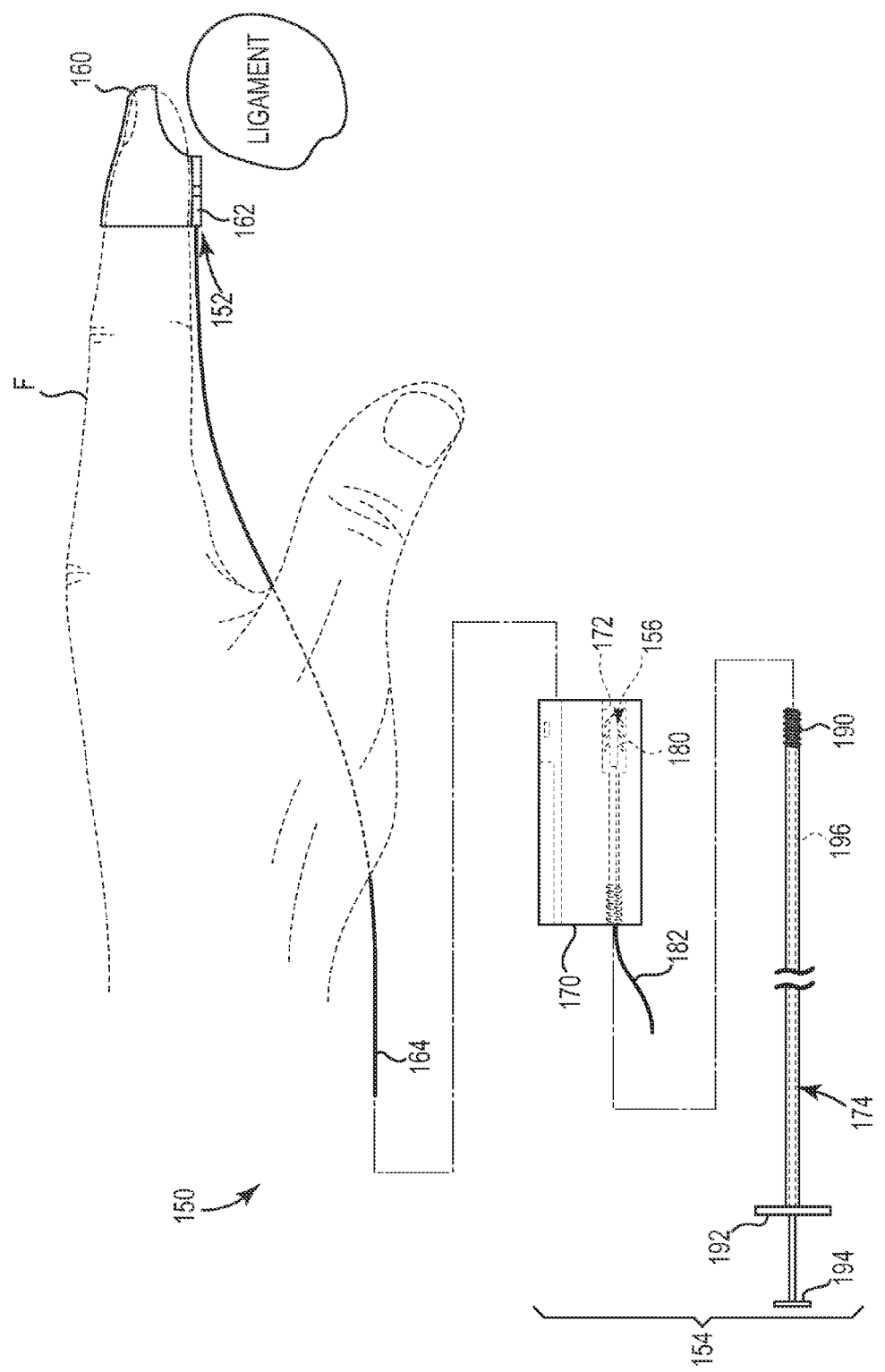
FIG. 1 is an exploded schematic view of one embodiment of a digital suture fixation system including an introducer and an anchor delivery device.

FIG. 1 is a side view of one embodiment of a digital suture fixation system 150. System 150 includes an introducer 152 that is attachable to a finger F, a delivery device 154 that is attachable to introducer 152, and an anchor 156 that is removably retained in the delivery device 154.

In one embodiment, introducer 152 includes a finger cot 160, a platform 162 attached to an exterior surface of finger cot 160, and a zip line 164 attached to platform 162. In one embodiment, delivery device 154 includes a car 170 configured to couple with and move along the zip line 164 and a shaft 174 that is configured to eject anchor 156 from car 170. The car 170 defines a port 172 sized to enclose anchor 156. In one embodiment, anchor 156 includes a barb portion 180 configured to engage with tissue and a suture line 182 trailing from barb portion 180. In one embodiment, the shaft 174 includes a distal end 190 that is attachable to the car 170, a proximal end 192 including a plunger 194, and a rod 196 that moves into and out of the shaft 174 in response to movement of the plunger 194.

System 150 is adapted to deliver anchor 156 to a landmark within the patient, where the landmark is not necessarily visible to the surgeon. For example, the finger cot 160 allows the finger F to identify the desired landmark, the car 170 is attachable to the platform 162 (which is located near a distal end of the finger F) to ensure that the anchor 156 is directed to the landmark identified by the finger F, and the shaft 174 is employed to selectively eject the anchor 156 into the landmark. Although the landmark in FIG. 1 is illustrated as a ligament, system 150 is configured to allow the surgeon to palpate and identify any of a variety of intracorporeal landmarks.

The systems disclosed in this specification are suited for the intracorporeal suturing of tissue during pelvic organ repair surgery, and in one embodiment are provided as sterile disposable surgical instruments that are discarded after the surgical procedure. To this end, the components of the systems are selected to be compatible with gas, steam, or radiation sterilization.

Figure 2:
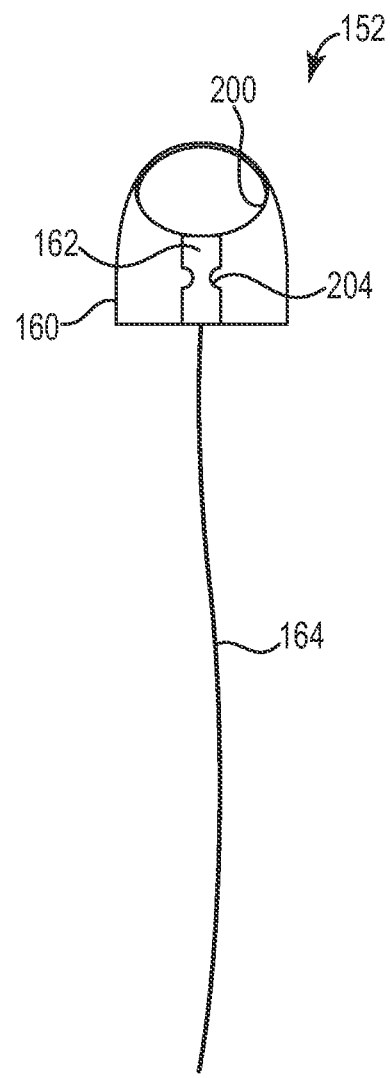
FIG. 2 is a bottom view of the introducer illustrated in FIG. 1.

FIG. 2 is a bottom view of introducer 152 showing zip line 164 trailing from a proximal end of introducer 152. In one embodiment, introducer 152 includes a window 200 formed in the finger cot 160 between platform 162 and a distal end of the finger cot 160. In one embodiment, the window 200 allows the finger F to directly contact tissue within a patient. In one embodiment, the window 200 allows a finger F inside of a glove (not shown) to identify a tissue landmark within a patient, where the glove is selected to provide the surgeon with a level of dexterity suited to sensing and discriminating different intracorporeal tissue landmarks. The platform 162 includes a retainer 204 that is configured to engage with the car 170 (FIG. 1) to secure the car 170 to the introducer 152. In one embodiment, the retainer 204 is provided as a pair of opposing substantially spherical recesses that are sized to receive spring-loaded ball bearings provided on the car 170.

Finger cot 160 is selected to be conformable to a distal end of the finger F, suitably elastic, and is suitably fabricated from plastic, metal, or combinations of plastic and metal (e.g., malleable metal thimbles covered with plastic as one example). Platform 162 is attached to finger cot 160 and is suitably formed from plastic, metal, or combinations of plastic and metal. Suitable suture line 182 materials include suture employed by surgeons in the treatment of pelvic organ prolapse, such as polypropylene suture, or the suture identified as Deklene, Deknatel brand suture, as available from Teleflex Medical, Mansfield, Mass., or suture available from Ethicon, a Johnson&Johnson Company, located in Somerville, N.J.

The zip line 164 is flexible and is suitably fabricated from a polymer strand, or a braided cable coated with plastic, as examples.

In one embodiment, introducer 152 is integrated into a distal finger sleeve of a glove, which allows the introducer 152 to be more closely associated with the surgeon's hand.

Figure 3:
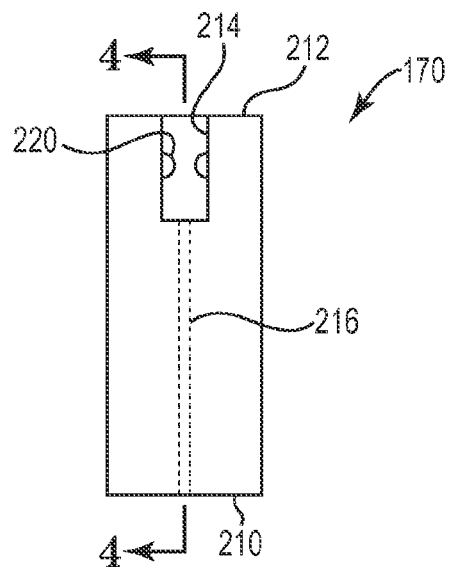
FIG. 3 is a top view of the delivery device illustrated in FIG. 1.
Figure 4:
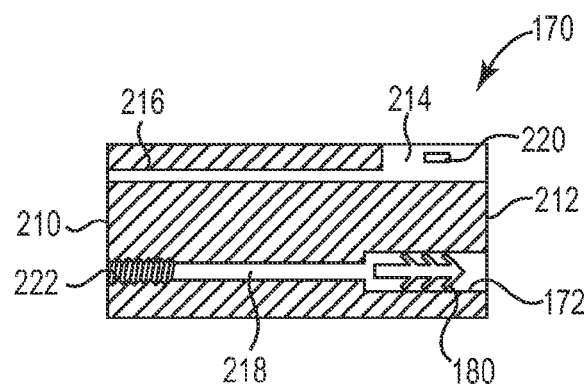
FIG. 4 is a cross-sectional view of the delivery device illustrated in FIG. 3.
Figure 5:
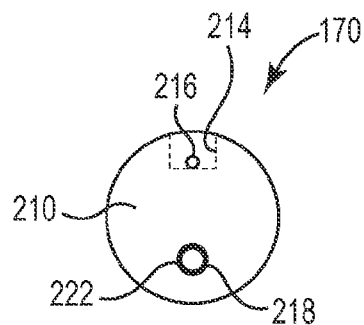
FIG. 5 is an end of view of the delivery device illustrated in FIG. 3.

FIG. 3 is a top view of car 170, FIG. 4 is a cross-sectional view of car 170, and FIG. 5 is a proximal end view of car 170. In one embodiment, car 170 includes a proximal end 210 opposite a distal end 212, a platform dock 214 formed adjacent to distal end 212, a zip line channel 216 extending between end 210 and dock 214, and a suture channel 218 extending between end 210 and port 172. The platform dock 214 includes a lock 220 configured to couple with retainer 204 to secure car 170 to platform 162 (FIG. 2). In one embodiment, the lock 220 includes spring-loaded ball bearings or another form of a biasing member configured to engage with recesses 204 formed on platform 162. The car 170 is configured to slide along the zip line 164 until lock 220 engages with retainer 204 to secure the car 170 to the platform 162.

In one embodiment, threads 222 are formed within a proximal end of suture line channel 218 and are sized to receive a threaded distal end 190 of shaft 174 (FIG. 1). In this manner, shaft 174 is configured to be removably attached to the car 170 such that rod 196 (FIG. 1) is aligned with suture line channel 218 and the barb portion 180 of anchor 156.

FIG. 5 is a proximal end view of car 170. In one embodiment, car 170 is substantially a circular cylinder, although other shapes and sizes that accommodate the intracorporeal delivery of the car 170 into the patient, as guided by the surgeon's preferences, are also acceptable.

FIGS. 6A-6D are side views of system 150 employed to insert an anchor into tissue according to one embodiment.

Figure 6A:
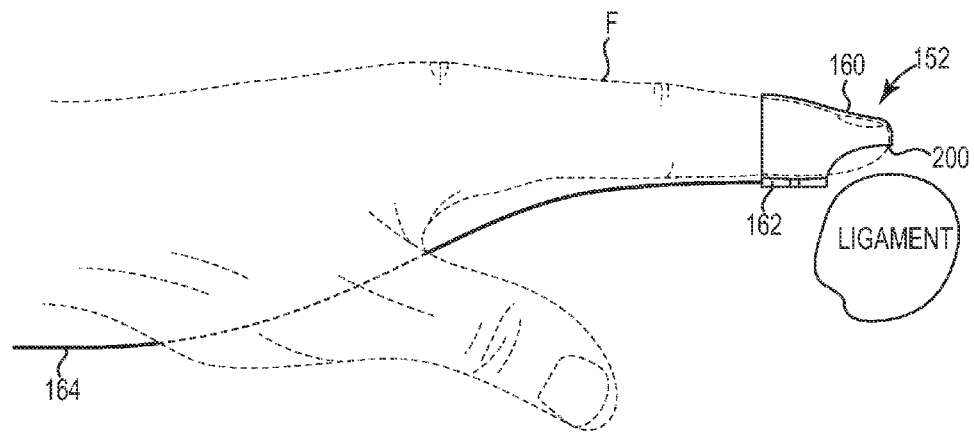
FIG. 6A is a side view of a finger wearing the introducer illustrated in FIG. 1.

FIG. 6A is a side view of introducer 152 placed over the finger F such that the finger F is available to palpate tissue through the window 200.

Figure 6B:
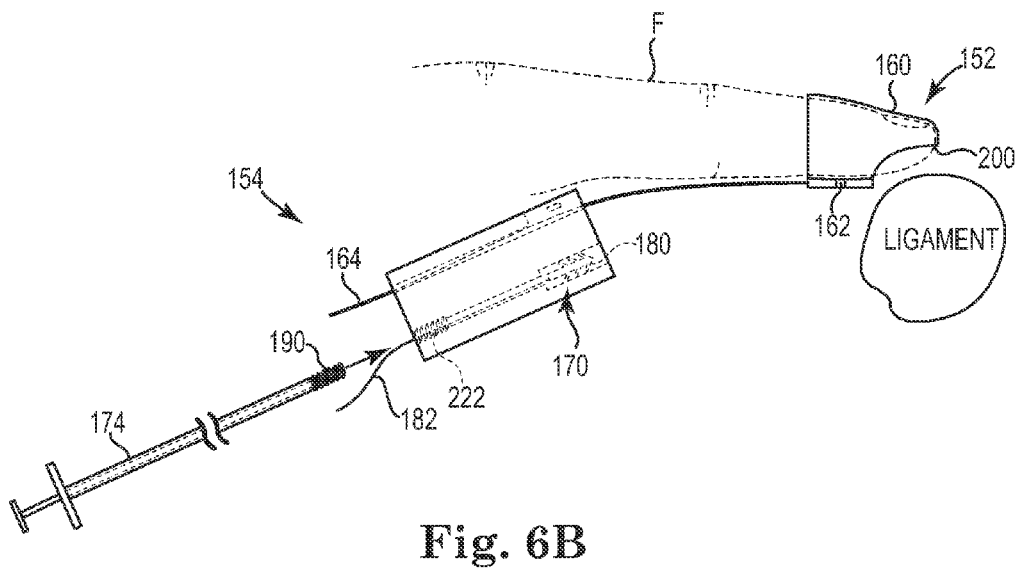
FIG. 6B is a side view of the delivery device illustrated in FIG. 3 shuttled along a zip line to the introducer illustrated in FIGS. 1 and 2.

FIG. 6B is a side view of car 170 and shaft 174 of delivery device 154 moving along a zip line 164 for engagement with platform 162. It is to be understood that shaft 174 could be suitably attached to car 170 before car 170 is engaged with the zip line 164 or after the car 170 is engaged with the zip line 164.

Figure 6C:
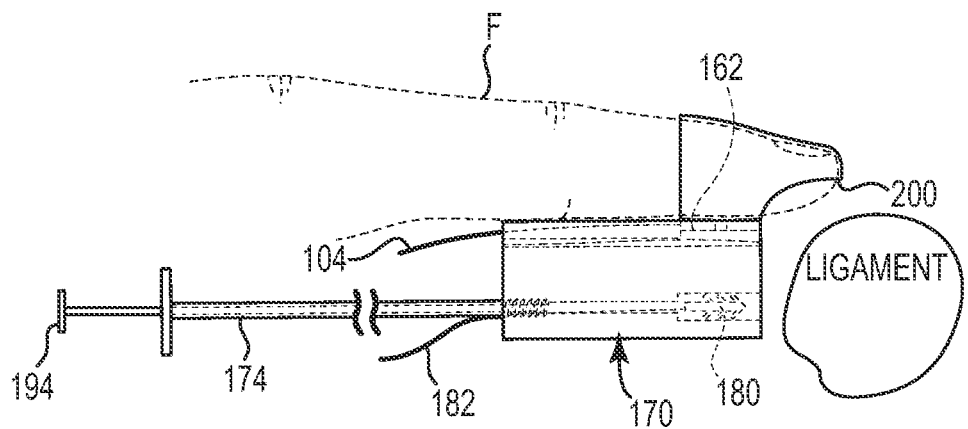
FIG. 6C is a side view of the system illustrated in FIG. 1 employed to deliver an anchor to tissue of a patient according to one embodiment.
Figure 6D:
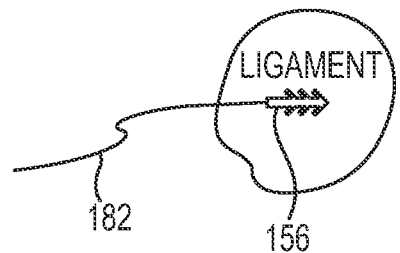
FIG. 6D is a schematic view of a suture line trailing away from the anchor that has been fixed into the tissue of the patient.

FIG. 6C is a side view of the car 170 engaged with the platform 162 and the shaft 174 connected to the car 170. In one embodiment, the barb portion 180 of the anchor 156 is retained within port 172 (FIG. 1) and suture line 182 trails from the proximal end 210 of the car 170 (FIG. 4). In this configuration, the shaft 174 is connected to the car 170, and the car 170 is connected to the platform 162, where the platform 162 and the car 170 are positioned adjacent to the window 200 and thus ready to deliver the barb portion 180 into the tissue (e.g., ligament) palpated by the finger F. In one embodiment, the surgeon uses the opposite hand (e.g., the hand to which introducer 152 is not attached) to activate the plunger 194, which drives the rod 196 (FIG. 1) axially from the shaft 174 to eject the barb portion 180 of the anchor 156 axially from the car 170 and into the ligament, as illustrated in FIG. 6D. Although the plunger 194 is illustrated as a push-activated mechanical device in FIG. 6C, other embodiments of the plunger 194 provide a plunger that operates pneumatically or electro-mechanically. Other suitable activation mechanisms for moving rod 196 to deliver anchor 156 include pull activation, twist activation, or squeeze activation of shaft 174 to activate movement of rod 196.

The anchor 156 is configured to penetrate tissue, including tough ligament tissue, and engage with the tissue after penetration. In one embodiment, the barb portion 180 is selectively deployed to expand from the anchor 156 only after the anchor penetrates into the tissue. In one embodiment, the barb portion 180 extends laterally from the anchor 156 and engages with the tissue as soon and the anchor penetrates into the tissue.

Figure 7:
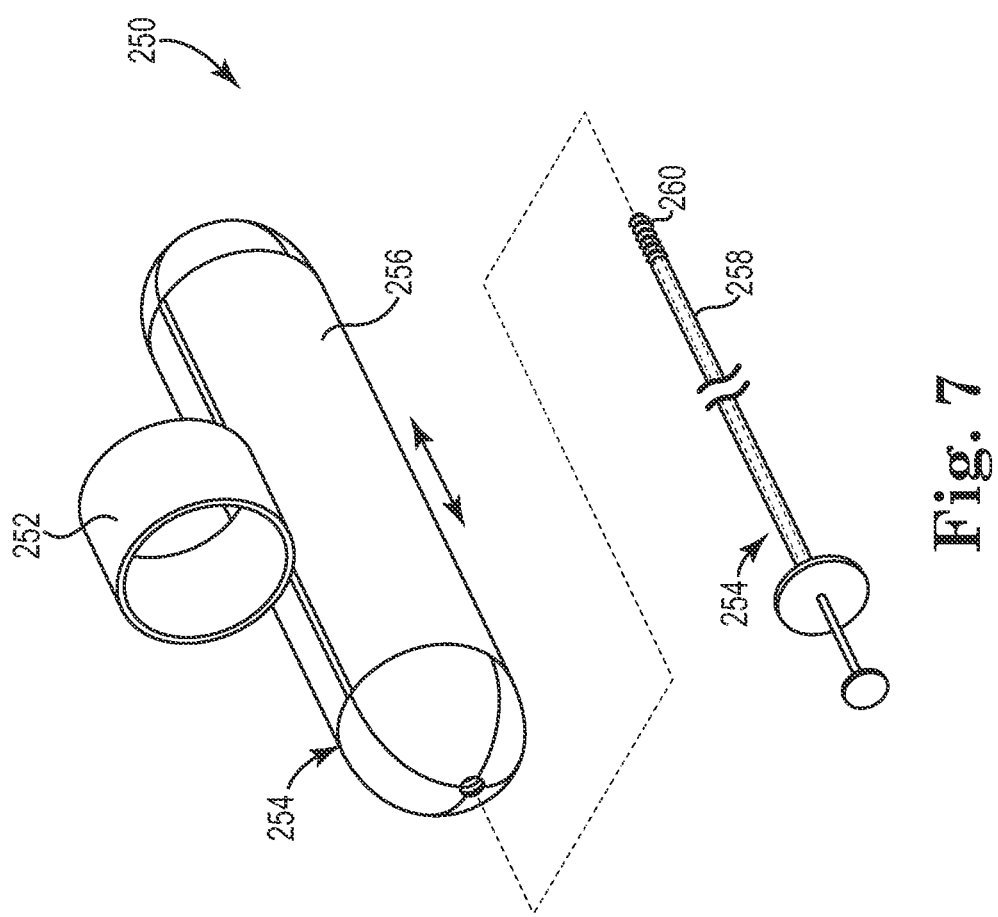
FIG. 7 is an exploded perspective view of a digital suture fixation system including an introducer and an anchor delivery device according to one embodiment.

FIG. 7 is a perspective view of another embodiment of a digital suture fixation system 250. In one embodiment, system 250 includes an introducer 252 that is attachable to a finger, a delivery device 254 attached to introducer 252, and an anchor (not shown) that is removably attachable to delivery device 254. In one embodiment, the introducer 252 is a band 252 that is attachable to the finger and the delivery device 254 and includes an anchor housing 256 attached to an exterior surface of the band 252. The delivery device 254 includes a shaft 258 having a distal end 260 that is configured to thread into a proximal end of the anchor housing 256. The anchor housing 256 is sized to retain an anchor (or an anchor and a suture line) and the shaft 258 is configured to deploy the anchor from the anchor housing 256.

FIG. 8A is a side view of system 250. The anchor housing 256 includes a channel 270 that is sized to receive anchor 156 and suture line 182. In one embodiment, anchor housing 256 has a longitudinal length between about 0.75-1.5 inches, and band 252 is configured to allow housing 256 to slide/move longitudinally (laterally left and right in the orientation of FIG. 8A). In this manner, the anchor housing 256 is sized to be positioned at a base segment of the finger (behind the distal-most joint of the finger) to allow the distal end of the finger freedom of movement. The anchor housing 256 is configured to move relative to the band 252 to a position adjacent to the distal end of the finger F to bring the anchor 156 near the desired landmark previously identified by the surgeon's finger F.

In one embodiment, the band 252 is provided as adjustable band including a buckle or other adjustable form of attachment. Suitable materials for fabrication of the band 252 include plastics, metals, or combinations of plastics and metals. In one embodiment, the anchor housing 256 is molded from plastic attached to the band 252. In one embodiment, shaft 258 is similar to shaft 174 (FIG. 1).

FIG. 8B is an exploded schematic view of shaft 258 moved distally forward and ready for engagement with anchor 156. In one embodiment, shaft 258 includes an extensible post 272 that is configured to extend out of a distal end 260 of shaft 258 to engage with a bore 274 formed in anchor 156. In this manner, the post 272 is configured to drive the anchor 156 axially out of the channel 270 and into the tissue of the patient.

Figure 9A:
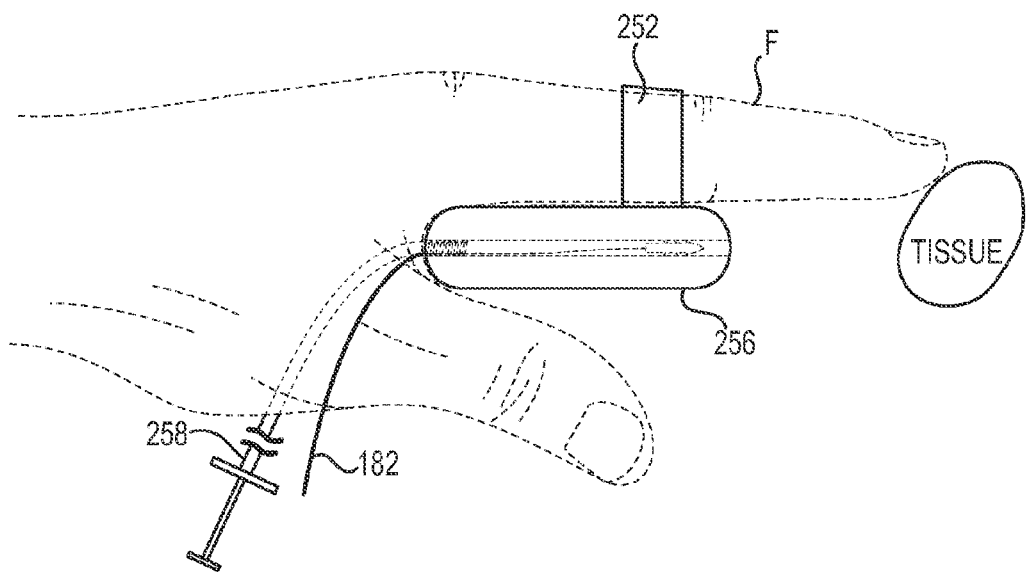
FIG. 9A is a side view of a finger wearing the system illustrated in FIG. 7.
Figure 9B:
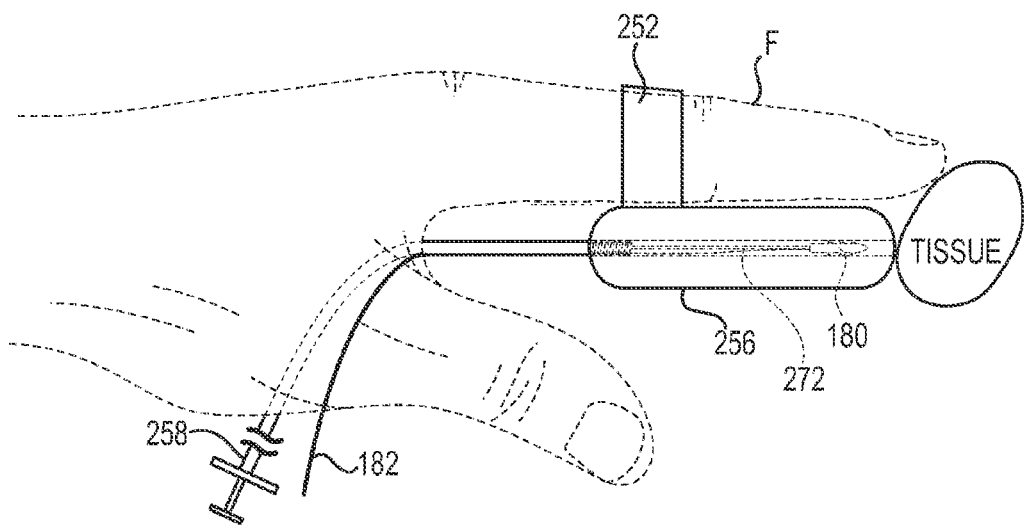
FIG. 9B is a side view of the delivery device illustrated in FIG. 7 delivered to a landmark inside of the patient's body.
Figure 9C:
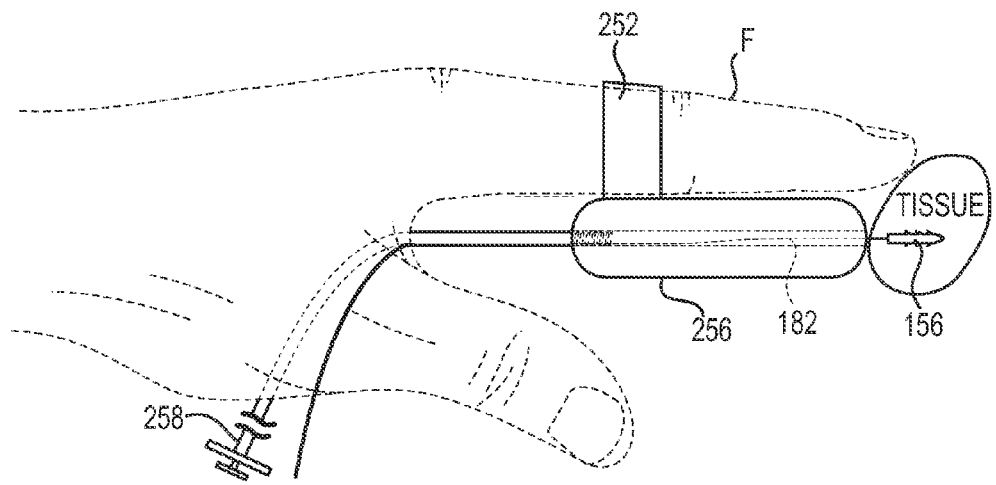
FIG. 9C is a side view of the system illustrated in FIG. 7 employed to deliver an anchor to the landmark inside of the patient's body.

FIGS. 9A-9C provides schematic views of system 250 employed to deliver an anchor into tissue.

FIG. 9A is a schematic view of the band 252 attached to the finger F in a manner that locates the anchor housing 256 at the base of the finger F near the web of the thumb. The distal end of the finger F is unimpeded by the anchor housing 256 and is thus free to palpate the tissue. The shaft 258 trails behind the anchor housing 256 out of the patient's body for access by the other hand (e.g., the right hand in this example).

The finger F is fully mobile (even if protected by a surgical glove) and able to palpate a desired tissue location for deployment of anchor 156. As illustrated in FIG. 9B, the anchor housing 256 is movable relative to the band 252 to position the distal end of the anchor housing 256 (retaining the anchor 156) next to the tissue landmark. In one embodiment, the shaft 258 is pushed in a proximal direction to displace the housing 256 proximally forward toward the tissue.

The anchor housing 256 is not drawn to scale. In one embodiment, it is desirable to provide the anchor housing 256 in a low-profile format (e.g. a flat elliptical shape) that is configured to lay flat against the palm of a user's hand. For example, in one embodiment the anchor housing 256 has a lateral cross-sectional size that is similar to the size of the diameter of the shaft 258 such that the shaft 258 and the housing 256 appear as a single cable.

FIG. 9C illustrates anchor 156 driven into the tissue by the post 272 (FIG. 8B) of the shaft 258. The suture line 182 is optional, and if provided, trails behind the anchor 156 through the anchor housing 256 and behind the hand of the surgeon. In one embodiment, the shaft 258 is rotated counterclockwise (one-quarter to one-half of a turn) to disengage the shaft 258 from the anchor 156. Thereafter, the surgeon retracts the finger F and the system 250 from the patient leaving the anchor 156 inserted into tissue and the suture line 182 trailing away from the anchor and out of the patient. The suture line 182 is tied off to reinforce or suture the pelvic floor of the patient. Alternatively, the suture line 182 serves as a conduit into the patient's body for delivery of support mesh intracorporeally to the inserted anchor 156.

Figure 9D:
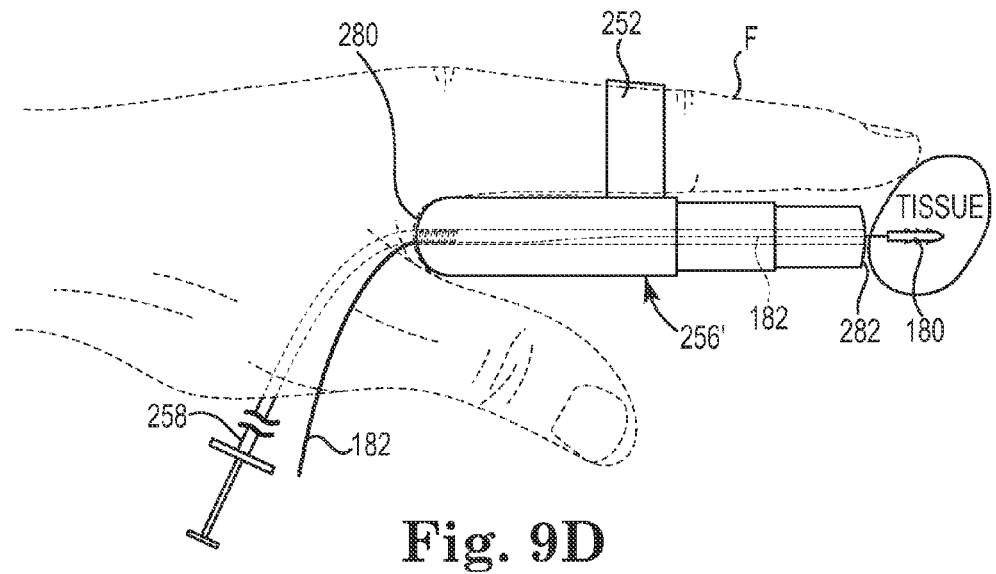
FIG. 9D is a side schematic view of a telescoping anchor housing.

FIG. 9D is a side schematic view of a telescoping anchor housing 256'. The telescoping anchor housing 256' has a proximal end 280 that nestles against a web of the hand and a distal end 282 that moves forward toward the distal end of the finger F when the shaft 258 is pressed into the proximal end 280 of the anchor housing 256'. The proximal end 280 contacts the webbing of the hand to allow the hand to drive the distal end 282 forcefully into the tissue to ensure that the anchor 156 penetrates tough tissue. Consistent with the above description, activation of the shaft 258 moves the post 272 in the axial forward direction to eject the anchor 156. In one embodiment, shaft 258 is attached to the proximal end 280 of the delivery device 256', the shaft 258 is pushed distally, and separating segments of the telescoping delivery device 256′ axially expand to drive anchor 180 into the tissue.

Figure 10:
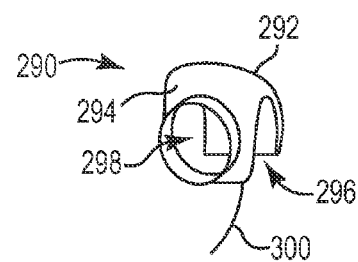
FIG. 10 is a perspective view of an optional position marker configured to be employed with the system illustrated in FIG. 7 according to one embodiment.

FIG. 10 is a perspective view of an optional position marker 290 configured for use with system 250. In one embodiment, position marker 290 includes a distal surface 292, a proximal surface 294, a slot 296 formed between the surfaces 292, 294, and a hole 298 formed in the proximal surface 294. In one embodiment, position marker 290 is provided as a stroke-length control and twist-release locator that is configured to be tacked into position by the anchor 156. For example, in one embodiment the hole 298 is sized to receive the distal end of anchor housing 256 (FIG. 8A) to allow accurate placement of the anchor 156 into the tissue. The position marker 290 functions to prevent inserting the anchor 156 too deeply into the tissue. The position marker 290 also functions to prevent twisting of the anchor 156 after placement of the anchor 156 to tissue. In one embodiment, position marker 290 includes another suture line 300 that is configured to trail out of the patient's body to a location that can be accessed by the surgeon for the subsequent delivery of support mesh into the patient to the location at which position marker 290 has been affixed.

Suitable materials for fabrication of position marker 290 include plastic or radio-opaque material.

Figure 11:
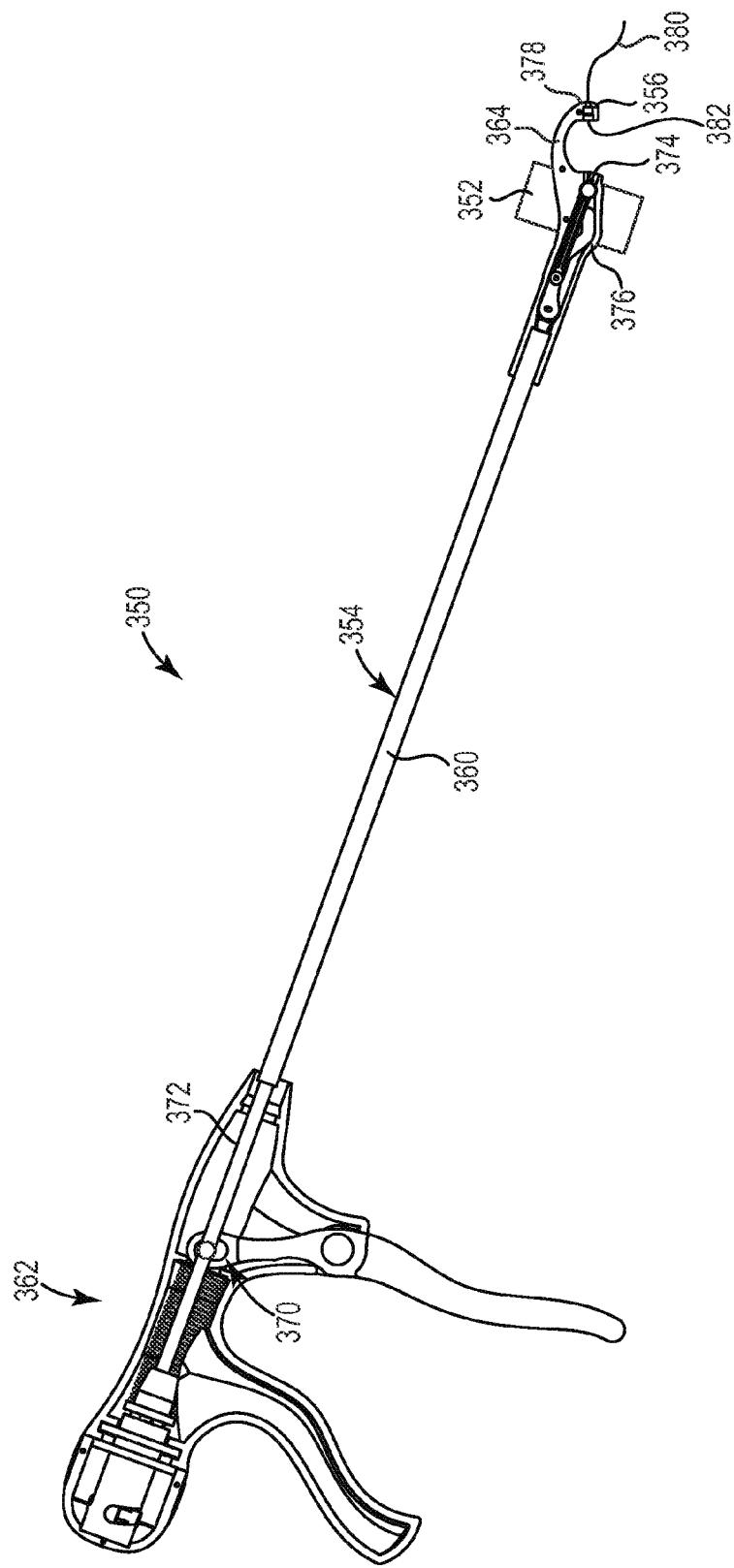
FIG. 11 is a side plan view of a digital suture fixation system including a delivery device attached to an introducer band according to one embodiment.

FIG. 11 is a side plan view of a digital suture fixation system 350 including an introducer band 352 that allows the surgeon to use a finger to precisely place a delivery device 354 next to a tissue landmark. The introducer band 352 is attachable to the finger F and a suture assembly 356 is retained by a head 364 of the delivery device 354. This configuration allows the finger F to guide the head 364 of the delivery device 354 directly and precisely to an intracorporeal tissue landmark (i.e., a target) identified by the finger F. The surgeon inserts his/her finger into the band 352 to guide the delivery device 354 through the dissected tissue precisely to the landmark previously identified by the finger, which positions the head 364 for delivery of the suture assembly 356 to the tissue landmark.

Delivery device 354 includes a shaft 360 coupled between a handle 362 and the delivery head 364. The introducer band 352 is attachable to the head 364. Handle 362 thus defines a proximal end of system 350 nearest a user of the system 350.

Figure 12A:
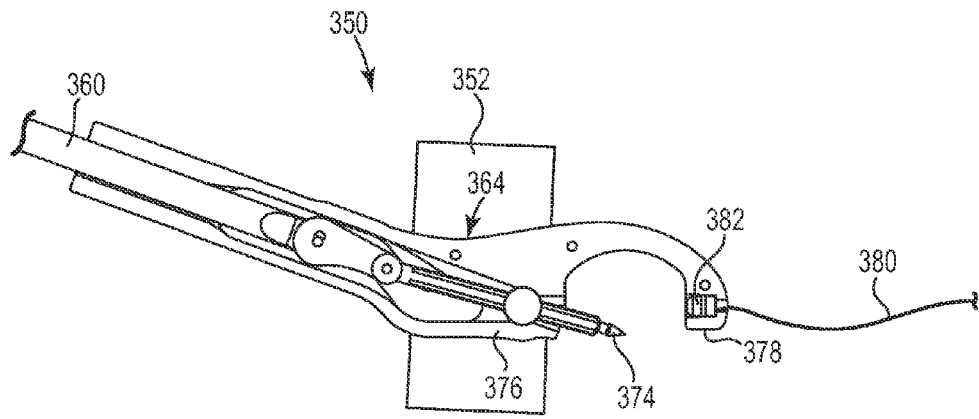
FIGS. 12A-12C are schematic cross-sectional views of the digital suture fixation system illustrated in FIG. 11 employed to throw a needle through tissue according to one embodiment.

With reference to FIGS. 11 and 12A, the needle 374 is stored within a proximal end portion 376 of the head 364 and the suture assembly 356 is stored within a distal end portion 378 of the head 364. The open space between the proximal end portion 376 of the head 364 and the distal end portion 378 of the head 364 is referred to as a throat. In one embodiment, the suture assembly 356 includes a suture line 380 connected to a capsule 382, and the capsule 382 is retained within distal end 378 of head 364. The needle 374 is adapted to move across the throat from the proximal end portion 376 of the head 364 to the distal end portion 378 of the head 364. The needle 374 is shaped to frictionally engage and mate with the capsule 382, remove the capsule 382 from distal end 378, and retract the capsule 382 into the proximal end portion 376 of head 364. In this manner, the suture line 380 is towed behind the capsule 382 and "thrown" through the tissue.

For example, handle 362 includes an actuator 370 communicating with a rod 372 that is disposed within shaft 360. The throat formed in the head 364 is configured to be engaged over a mass of tissue. When actuator 370 is activated (for example with the surgeon's free hand exterior to the patient), the rod 372 moves through shaft 360 to extend the needle 374 stored within the proximal end portion 376 of head 364 axially outward through tissue and toward the distal end 378 of head 364. Thus, the needle 374 moves away from the user (who is holding handle 362 at the proximal end of system 350) and is thrust through the tissue toward distal end 378 of system 350. The needle 374 ultimately grasps the capsule 382, and the needle 374 and the capsule 382 are pulled back through the channel formed in the tissue by the needle 374. Retraction of the needle 374 pulls the suture line 380 through the tissue, to "throw" the suture line through the tissue.

Figure 12B:
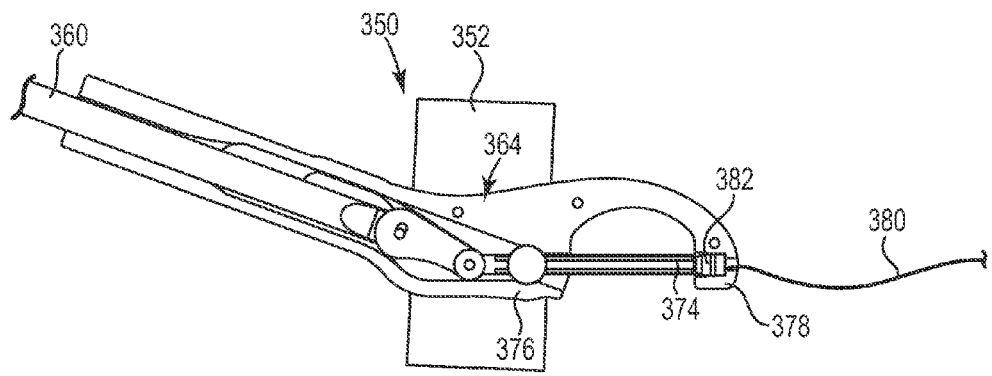
Figure 12C:
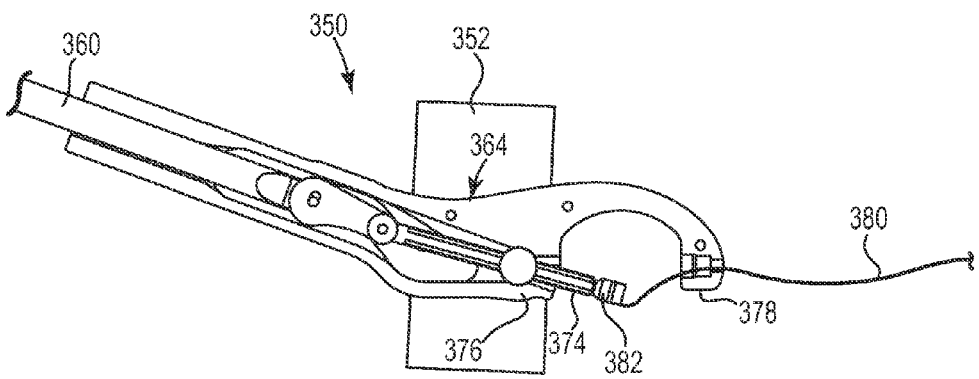

FIGS. 12A-12C are schematic cross-sectional views of digital suture fixation system 350 employed to throw needle 374 and capsule 382/suture 380 through tissue.

FIG. 12A is a schematic cross-sectional view of needle 374 partially extending from the proximal end portion 376 of head 364 after activation of actuator 370 (FIG. 11). Capsule 382 is seated in a cavity formed in the distal end 378 of head 364. It is recommended that the surgeon direct a trailing end of suture 380 over distal end 378 of head 364 and back toward a proximal end of shaft 360 (FIG. 11) for ease of managing the suture assembly during the procedure. To this end, in one embodiment the handle 362 is provided with a reel configured to receive the suture 380. For example, in one embodiment the suture 380 is retained on a suture cartridge, and the handle 362 is provided with a spindle configured to receive and retain the suture cartridge.

FIG. 12B is a schematic cross-sectional view of head 364 illustrating the needle 374 moved across the throat of head 364 and engaged with capsule 382. It is to be understood that the throat would typically be placed over a mass of tissue that the surgeon desires to suture. The needle 374 is reversible and configured to retract capsule 382 back in a proximal direction into the needle exit port of the proximal end portion 376 of head 364.

FIG. 12C is a schematic view of needle 374 and the capsule 382 partially retracted into the proximal end portion 376 of head 364. The needle 374 is retracted until the capsule 382 is parked inside the needle exit port of the proximal end portion 376 of head 364 and the suture 380 extends across the throat of head 364.

System 350 is suited for the intracorporeal suturing of tissue during pelvic organ repair surgery, and in one embodiment is provided as a sterile disposable surgical instrument that is discarded after the surgical procedure. To this end, the components of system 350 are selected to be compatible with gas, steam, or radiation sterilization.

Figure 13:
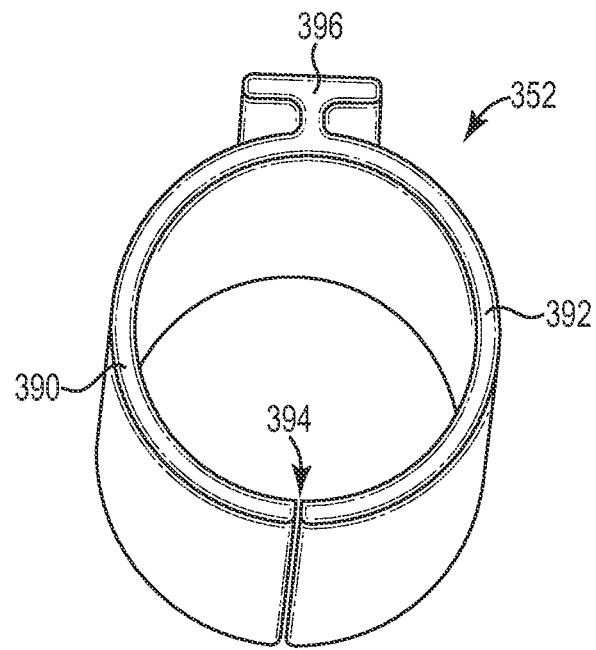
FIG. 13 is a perspective view of the introducer band illustrated in FIG. 11.

FIG. 13 is a perspective view of the introducer band 352. In one embodiment, the introducer band 352 is a discontinuous band defined by a first ring segment 390 separated from a second ring segment 392 by a space 394 and includes a flange 396 that is configured to be removably attached to the head 364 of delivery device 354 (FIG. 11). In one embodiment, the first and second ring segments 390, 392 are curved to define a substantially circular band sized to flexibly fit around a finger of a surgeon. The space 394 permits the ring segments 390, 392 to flex and adjust around differently sized fingers. The introducer band 352 is adapted to be placed over a finger of the surgeon to direct the head 364 of the delivery device 354 to a tissue landmark. The distal end of the finger of the surgeon is unencumbered and free to palpate tissue of the patient while the band 352 holds the delivery device 354 at the ready for placement of suture 380 and capsule 382.

In one embodiment, the introducer band 352 is molded from plastic. In one embodiment, the introducer band 352 includes a metal core (such as aluminum) having a plastic (such as silicone) molded over the metal core.

Figure 14:
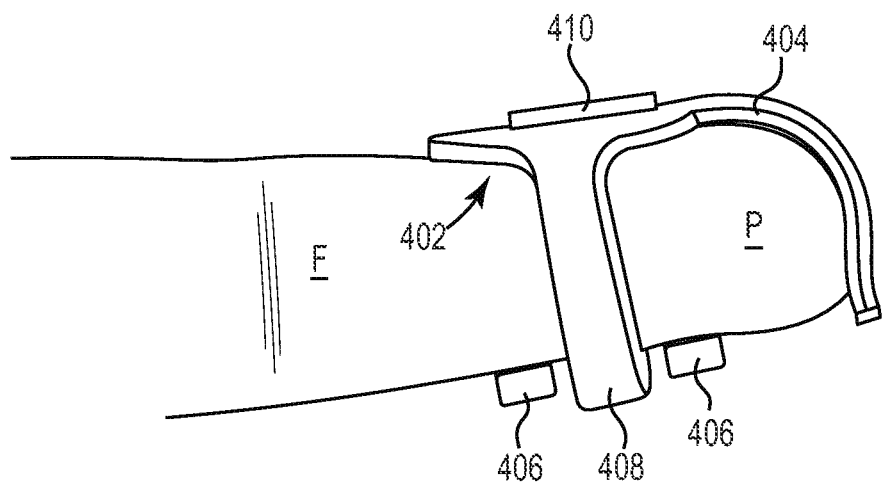
FIG. 14 is a perspective view of another embodiment of an introducer band.

FIG. 14 is a perspective view of another embodiment of an introducer band 402. FIG. 14 is oriented such that the view is directed to the pad P of the finger F, and an outside surface of the index finger F is oriented in the up direction. That is to say, FIG. 14 is a depiction of a pad of a left hand index finger.

In one embodiment, the introducer band 402 includes a base 404, a first pair of arms 406 that are configured to wrap a portion of the way around the finger F, a single arm 408 that is configured to wrap a portion of the way around the finger F in a direction opposite the first pair of arms 406, and a metal interface 410 attached to the base 404. In one embodiment, the metal interface 410 is a ferrous metal that is configured to magnetically couple with a magnet that is provided inside of the head 364 of the delivery device 354 (FIG. 11).

The introducer band 402 is malleable and configured to conform around a finger of the surgeon. In one example, the introducer band 402 is fabricated from a malleable sheet of metal that is over molded with a plastic coating, such as a core of 3003 series aluminum that is over molded with silicone.

When the introducer band 402 is donned, the pad P of the finger F is exposed and available for palpating tissue to locate a desired landmark within a patient. Thereafter, the surgeon magnetically attaches the head 364 of the delivery device 354 (FIG. 11) to the metal interface 410 of the introducer band 402, and using the finger F, digitally delivers the head 364 to the landmark.

Figure 15:
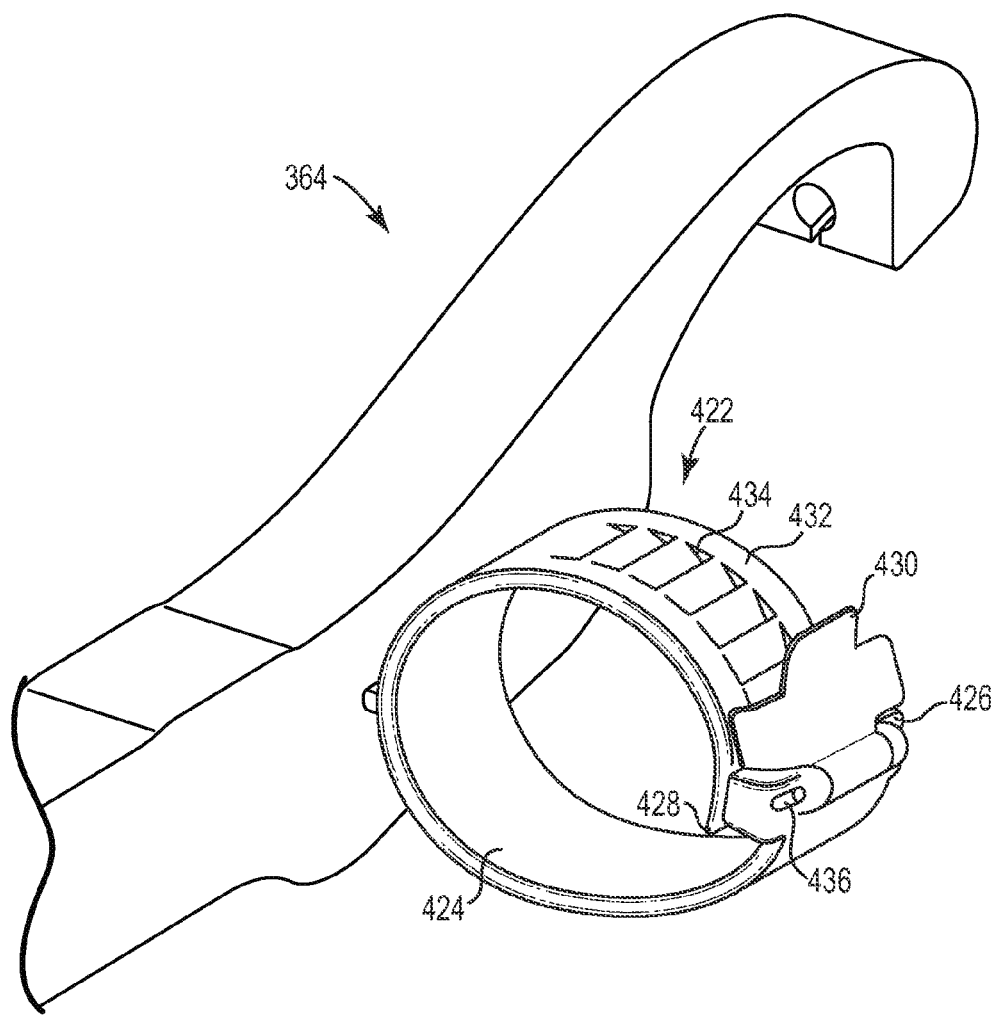
FIG. 15 is a perspective view of another embodiment of an introducer band attached to the delivery device illustrated in FIG. 11.

FIG. 15 is a perspective view of another embodiment of an introducer band 422 attached to the head 364 of the delivery device 354 (FIG. 11). In one embodiment, the introducer band 422 includes a belt 424 having a buckle end 426, a free end 428, and a buckle 430 configured to selectively engage the free end 428 of the belt 424. In one embodiment, an exterior surface 432 of the belt 424 includes engagement recesses 434 that allow the buckle 430 to adjustably engage the belt 424 around a finger of the user. In one embodiment, the belt 424 is fabricated from plastic and the buckle 430 moves about a pin 436.

During use, the surgeon will use a finger to palpate a desired landmark within a patient prior to donning the introducer band 422. Thereafter, the band 422 is attached to the finger to allow the finger to guide the head 364 of the delivery device 354 (FIG. 11) directly to the identified landmark. In one embodiment, the introducer band 422 is attached to the surgeon's finger and the surgeon subsequently uses the finger to palpate a desired landmark within a patient.

Figure 16:
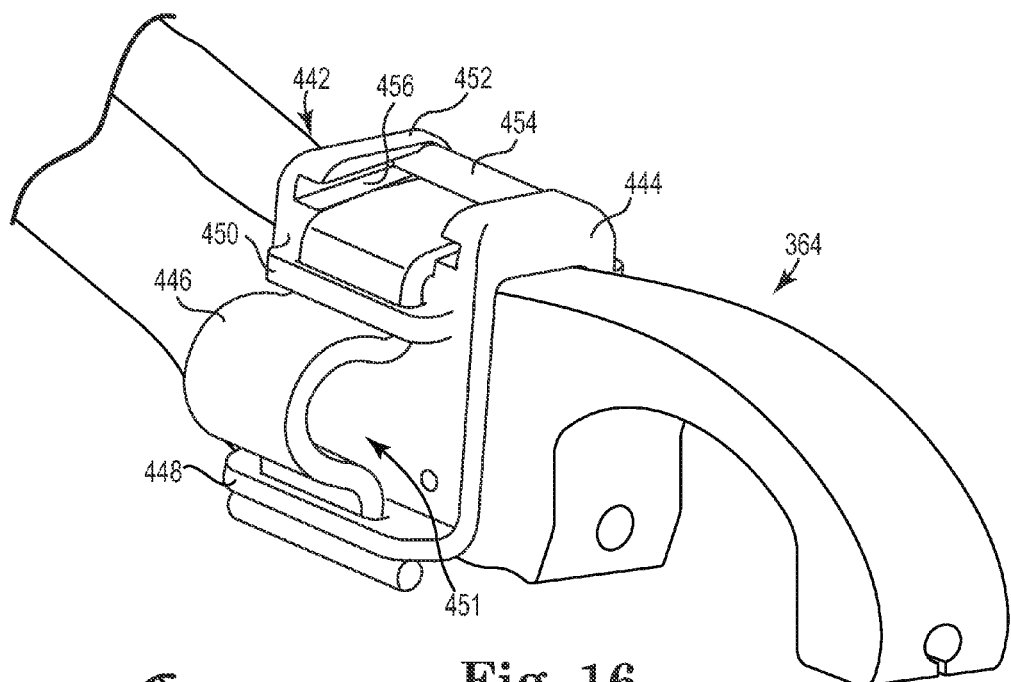
FIG. 16 is a perspective view of another embodiment of an introducer band attached to the delivery device illustrated in FIG. 11.

FIG. 16 is a perspective view of another embodiment of an introducer band 442 attached to the head 364 of the delivery device 354 (FIG. 11). In one embodiment, the introducer band 442 includes a shell 444 that is sized to receive the head 364 and a belt 446 that slides between two opposed flanges 448, 450 to form a finger slot 451. In one embodiment, a belt stop 452 is provided that includes a post 454 that slides within an angled slot 456 to allow the selective adjustment of the belt 446 around the finger F. The belt stop 452 is configured to prevent the band 446 from sliding through the flange 450, which would undesirably result in the finger slot 451 expanding after it is had been sized to fit around the finger of the surgeon.

Figure 17:
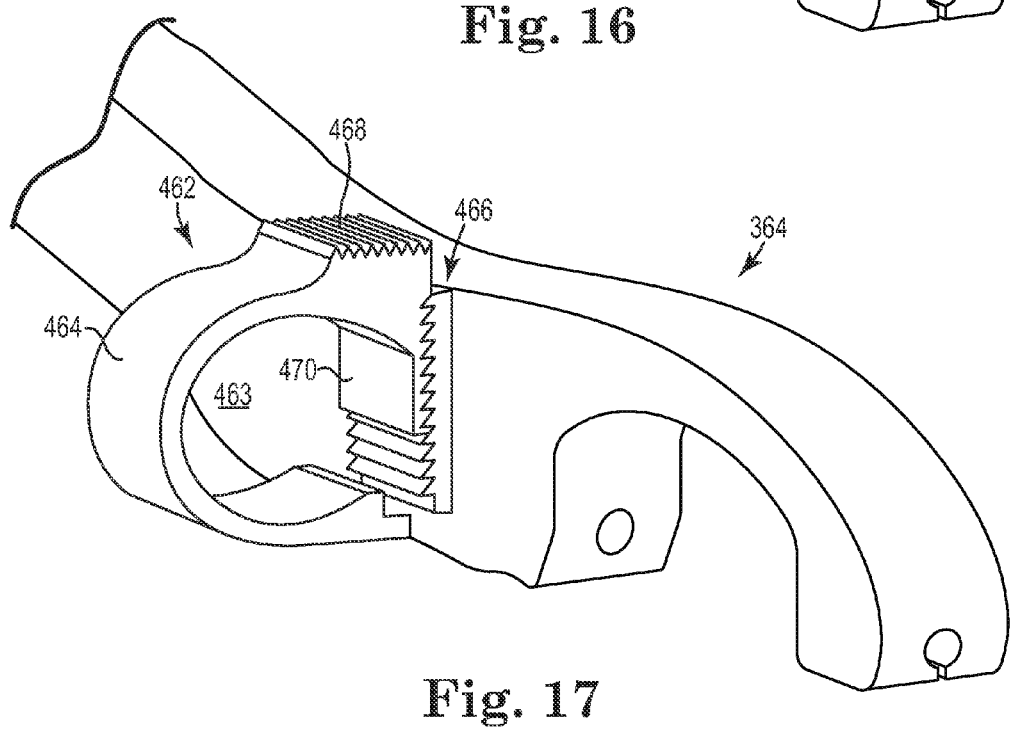
FIG. 17 is a perspective view of another embodiment of an introducer band attached to the delivery device illustrated in FIG. 11.

FIG. 17 is a perspective view of another embodiment of an introducer band 462 attached to the head 364 of the delivery device 354 (FIG. 11). In one embodiment, the introducer band 462 is integral with the head 364. An adjustable finger slot 463 is provided by a belt 464 that is formed to extend from a base of the delivery head 364 and terminate at an adjustable engagement slide 466. In one embodiment, the belt 464 includes a pressure platform 468 that allows the belt 464 to be adjusted by movement of one end 470 of the belt 464 relative to the engagement slide 466. In one embodiment, the engagement slide 466 is provided with a saw tooth pattern that is configured to mesh with saw teeth provided on the end 470 of the belt 464 to provide an adjustable and removable locking mechanism. Alternatively, the engagement slide 466 is provided with a hook-and-loop form of adjustable attachment. In one embodiment, the introducer band 462 is integrally formed as a complement of the delivery head 364.

Embodiments of digital suture fixation systems have been described that include a digital introducer that is attachable to a finger to guide an anchor delivery device intracorporeally to a patient. The introducer is attachable to the finger in one of a variety of approaches, include attachment bands, magnetic attachment mechanisms, finger cots, attachment strands such as zip tie style strands, etc. The introducer is configured to allow the finger to palpate and identify a landmark within a patient and the delivery device is configured to insert an anchor or a suture attached to an anchor or capsule into the landmark. Thus, accurate placement of the anchor/suture is provided even if the landmark is not visible to the surgeon.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A suture fixation system comprising:
    a suture assembly comprising an anchor;
    an introducer that is attachable to a finger of a person, the introducer comprising a platform and a zip line attached to the platform, the zip line is one of a polymer strand and a cable; and
    a delivery device including a first channel sized to receive the zip line, the first channel provided to allow the delivery device to move over the zip line, the delivery device including a second channel sized to receive and removably retain the anchor;
    wherein the introducer allows the finger to identify a target landmark within a patient and the delivery device is movable along the zip line and attachable to the platform to position the anchor for insertion to the target landmark.

2. The suture fixation system of claim 1, wherein the anchor is a tissue penetrating anchor comprising a tissue penetrating barb extending from a flange and the suture assembly comprises a suture line connected to the flange.

3. The suture fixation system of claim 1, wherein the target landmark is an intracorporeal landmark and the zip line extends from the intracorporeal landmark to a location outside of the patient.

4. The suture fixation system of claim 1, wherein the second channel of the delivery device includes a port that is sized to enclose the anchor.

5. The suture fixation system of claim 4, wherein the suture fixation system further comprises:
    a shaft that is attachable to the delivery device and a rod disposed in the shaft.

6. The suture fixation system of claim 5, wherein the rod is movable within the shaft to axially eject the anchor from the port.

7. The suture fixation system of claim 1, wherein the introducer comprises a finger cot attachable to a distal tip of the finger, the platform attached to an exterior of the finger cot.

8. The suture fixation system of claim 7, wherein the finger cot defines a window sized to allow the distal tip of the finger to touch the target landmark, the platform located proximal the window.

9. The suture fixation system of claim 1, wherein the platform includes a lock that is operable to lock the delivery device to the platform.

10. The suture fixation system of claim 9, wherein the lock includes a biasing member.

11. The suture fixation system of claim 9, wherein the lock includes spring-loaded ball bearings.

\* \* \* \* \*